United States Patent [19]

Cooper et al.

[11] Patent Number: 4,727,076
[45] Date of Patent: Feb. 23, 1988

[54] TETRAHYDROQUINOLINYLALKYL AMINO PYRIDONES AND RING HOMOLOGUES THEREOF, USEFUL AS HISTAMINE-$H_1$-RECEPTOR ANTAGONISTS

[75] Inventors: David G. Cooper, Letchworth; George S. Sach, Welwyn, both of England

[73] Assignee: Smith Kline & French Laboratories Ltd., Welwyn Garden City, England

[21] Appl. No.: 5,706

[22] Filed: Jan. 21, 1987

[30] Foreign Application Priority Data

Jan. 25, 1986 [GB] United Kingdom ............... 8601816

[51] Int. Cl.[4] .................. A61K 31/505; C07D 239/22
[52] U.S. Cl. ..................................... 514/272; 544/320; 544/321
[58] Field of Search ................. 544/320, 321; 514/272

[56] References Cited

U.S. PATENT DOCUMENTS

| | | | |
|---|---|---|---|
| 4,154,834 | 5/1979 | Brown et al. | 544/320 |
| 4,255,428 | 3/1981 | Brown et al. | 544/320 |
| 4,385,058 | 5/1983 | Cooper et al. | 544/320 |
| 4,444,772 | 4/1984 | Sach | 544/320 |
| 4,486,434 | 12/1984 | Sach | 544/320 |
| 4,537,890 | 8/1985 | Sach | 544/320 |
| 4,537,891 | 8/1985 | Sach | 544/320 |
| 4,547,506 | 10/1985 | Ife | 544/320 |
| 4,548,940 | 10/1985 | Ife | 544/320 |

*Primary Examiner*—Henry R. Jiles
*Assistant Examiner*—J. Richter
*Attorney, Agent, or Firm*—Linda E. Hall; Janice E. Williams; Alan D. Lourie

[57] ABSTRACT

The invention provides tetrahydroquinolinylalkylamino pyrimidones, and ring homologues thereof, of the general formula (1):

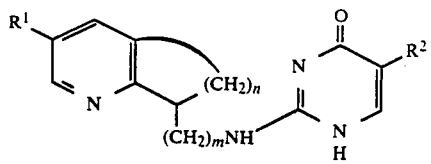

wherein $R^1$ is hydrogen or an alkyl, alkoxy, halogen or amino-substituent, m and n are each 2, 3 or 4 and $R^2$ is hydrogen, alkyl or variously substituted benzyl.

The compounds are useful as histamine-$H_1$-receptor antagonists.

9 Claims, No Drawings

TETRAHYDROQUINOLINYLALKYL AMINO PYRIDONES AND RING HOMOLOGUES THEREOF, USEFUL AS HISTAMINE-$H_1$-RECEPTOR ANTAGONISTS

This invention relates to certain pyridine derivatives, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines") histamine $H_1$-antagonists) a common example of which is mepyramine.

According to the present invention there are provided compounds of formula (1):

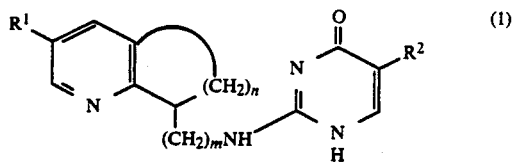

and pharmaceutically acceptable acid addition salts thereof, in which $R^1$ is hydrogen, $C_{1-4}$alkyl, $C_{1-4}$alkoxy, halogen or amino;

n is 2, 3 or 4;

m is 2, 3 or 4; and $R^2$ is hydrogen or $CH_2R^3$ where $R^3$ is hydrogen, $C_{1-6}$alkyl, or $C_{3-8}$cycloalkyl; phenyl optionally substituted by one or more $C_{1-6}$alkyl, $C_{1-6}$alkoxy, nitro or hydroxy groups or halogen atoms, or a methylenedioxy group; pyridyl or pyridyl-N-oxide optionally substituted by one or more $C_{1-6}$alkyl, $C_{1-6}$alkoxy, hydroxymethyl or hydroxy groups or halogen atoms; or a pyridone group in which the nitrogen atom is substituted by $C_{1-6}$alkyl.

Examples of alkyl groups for $R^1$ and $R^2$ and the optional substituents in $R^3$ are methyl, ethyl and n-propyl.

Examples of alkoxy groups for $R^1$ and the optional substituents in $R^3$ are methoxy, ethoxy and n-propoxy.

Examples of halogens for $R^1$ and the optional substituents in $R^3$ are fluorine, chlorine and bromine.

$R^1$ can be hydrogen, $C_{1-4}$alkyl, particularly methyl, or halogen, particularly bromine.

Preferably $R^1$ is hydrogen.

Preferably n is 3.

Preferably m is 3.

Preferably $R^2$ is $CH_2R^3$.

When $R^3$ is $C_{1-6}$alkyl, it can be methyl or propyl.

Examples of $C_{3-8}$cycloalkyl groups for $R^3$ are cyclopentyl and cyclohexyl.

When $R^3$ is optionally substituted phenyl or pyridyl, preferably the phenyl or pyridyl moiety contains a maximum of two substituents.

Examples of optionally substituted phenyl groups for $R^3$ are phenyl, 2-chlorophenyl, 3-chlorophenyl, 4-chlorophenyl, 3,4-dichlorophenyl, 2-bromophenyl, 3-bromophenyl, 4-bromophenyl, 4-fluorophenyl, 4-methylphenyl, 4-methoxyphenyl, 4-hydroxyphenyl, 3-nitro-4-hydroxyphenyl and 3,4-methylenedioxyphenyl.

When $R^3$ is an optionally substituted pyridyl group it can be an optionally substituted 2-, 3- and 4-pyridyl group. Examples of optionally substituted pyridyl groups for $R^2$ are 2-pyridyl, 5-fluoro-2-pyridyl, 5-chloro-2-pyridyl, 5-bromo-2-pyridyl, 3-pyridyl, 4,6-dimethyl-3-pyridyl, 5,6-dimethyl-3-pyridyl, 4-pyridyl and in particular 6-methyl-3-pyridyl.

When $R^3$ is an N-alkyl pyridone group it can be 1-alkyl-2-oxopyrid-5-yl, 1-alkyl-2-oxopyrid-3-yl, 1-alkyl-4-oxopyrid-3-yl, 1-alkyl-2-oxopyrid-4-yl, 1-alkyl-2-oxopyrid-6-yl or 1-alkyl-4-oxopyrid-2-yl.

Preferably $R^3$ is 3-pyridinyl-N-Oxide, 6-methyl-3-pyridinyl-N-Oxide, 6-hydroxymethyl-3-pyridyl, 4,6-dimethyl-3-pyridinyl-N-Oxide, 6-hydroxymethyl-4-methyl-3-pyridyl, 5,6-dimethyl-3-pyridinyl-N-Oxide 6-hydroxymethyl-5-methyl-3-pyridyl, 4-pyridinyl-N-Oxide, 6-methyl-3-pyridyl, or 1-methyl-2-oxo-pyrid-4-yl.

Examples of compounds within the scope of this invention are:

2-[3-(5,6,7,8-tetrahydroquinol-8-yl)propylamino]-5-[pyrid-4-yl-methyl-N-Oxide]-pyrimidine-4-one.

2-[3-(5,6,7,8-tetrahydroquinol-8-yl)propylamino]-5-(6-methylpyrid-3-ylmethyl)-4(1H)-pyrimidone 2-[3-(5,6,7,8-tetrahydroquinol-8-yl)propylamino]-5-(6-methyl-N-oxo-pyrid-3-ylmethyl)-4(1H)-pyrimidone 2-[3-(5,6,7,8-tetrahydroquinol-8-yl)propylamino]-5-(6-hydroxymethylpyrid-3-ylmethyl-4(1H)-pyrimidone.

The compounds of formula (1) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

The compounds of formula (1) exhibit optical activity and all isomers in resolved and racemic forms are included within the scope of this invention.

The compounds of formula (1) in which $R^3$ is pyridyl substituted by hydroxy can also exist in the tautomeric dihydro-oxo-pyridyl form. The compounds of formula (1) can also exist in the pyrimidin-6-one and 4-hydroxypyrimidine tautomeric forms. All these tautomeric forms are included within the scope of this invention.

Compounds of formula (1) can be made by reacting an amine of formula (2):

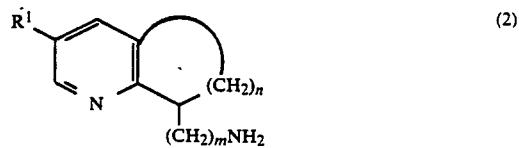

where $R^1$, n and m are as defined with reference to formula (1) (where $R^1$ is optionally protected if it is an amino group);

with a compound of formula (3):

where
R⁴ is a group displaceable with amine; and
R⁵ is hydrogen or CH₂R⁶ where

R⁶ is hydrogen; $C_{1-6}$alkyl; $C_{3-8}$cycloalkyl; phenyl optionally substituted by one or more $C_{1-6}$ alkyl, $C_{1-6}$alkoxy, nitro, hydroxy or protected hydroxy groups or halogen atoms, or a methylenedioxy group; pyridyl or pyridyl-N-oxide optionally substituted by one or more $C_{1-6}$alkyl, $C_{1-6}$alkoxy, hydroxymethyl or protected hydroxy groups or halogen atoms; or a pyridone group in which the nitrogen atom is substituted by $C_{1-6}$alkyl;

and thereafter removing any amino or hydroxy protecting groups; optionally converting the compound of formula (1) so obtained where $R^2$ is an N-oxo-6-methylpyridyl group into the corresponding compound of formula (1) where $R^2$ is a 6-hydroxymethylpyridyl group; and thereafter optionally converting the compound of formula (1) so obtained into a salt.

Examples of groups R⁴ are $C_{1-6}$alkylthio (particularly methylthio), benzylthio, chlorine, bromine and nitroamino. Preferably R⁴ is nitroamino.

This reaction can be carried out at an elevated temperature in the absence of a solvent, for example at from 80° to 170°, preferably from 120° to 140°, or in a solvent at an elevated temperature, for example at the reflux temperature of the reaction mixture. The choice of solvent is affected by solubility characteristics of the reactants. Preferably the solvent is pyridine, a picoline or mixture of picolines, a $C_{1-6}$alkanol, preferably ethanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide or sulpholane.

Examples of hydroxy protecting groups are methoxymethyl, methylthiomethyl, tetrahydropyranyl, arylmethyl, for example benzyl, $C_{1-6}$alkyl, for example methyl, and alkanoyl, for example formyl or acetyl. These protecting groups can be removed by standard methods, for example where the protecting group is $C_{1-6}$ alkanoyl or $C_{1-6}$alkyl, by acid or basic hydrolysis. The use of protecting groups is discussed in J. F. McOmie, Protective Groups in Organic Chemistry, 1973, Plenum Press, IBSN 0-306-30717-0.

The compounds of formula (1) where $R^3$ is a N-oxo-6-methylpyridyl group can be converted into the corresponding compound of formula (1) where $R^3$ is 6-hydroxymethylpyridyl by reacting with an organic anhydride for example trifluoroacetic anhydride.

Pharmaceutically acceptable salts of compounds of formula (1) can be prepared by standard methods, for example by reacting a solution of the compound of formula (1) with a solution of the acid.

The amines of formula (2) in which $R^1$ is other than halogen can be prepared by reacting a compound of formula (4):

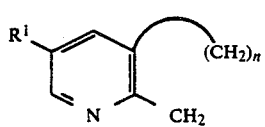

(4)

where $R^1$ is hydrogen, $C_{1-4}$alkyl, $C_{1-4}$alkoxy or amino, and n is as defined for formula (1), with a compound of formula (5)

$$X(CH_2)_mR^7 \quad (5)$$

where m is as defined with reference to formula (1), X is halogen, $R^7$ is amino or a protected amino group, in the presence of a strong base and thereafter removing any amino protecting group.

Examples of strong bases are alkali metal hydrides, particularly sodium hydride. The reaction is carried out in the presence of a polar solvent for example dimethylsulphoxide. Preferably $R^7$ is amino and the reaction is carried out using sodamide in liquid ammonia.

In formula (5) X can be chlorine, bromine or iodine. Preferably X is chlorine when sodamide is the base.

The protected amino group can be converted into amino by standard methods, for example when it is phthalimido by reaction with concentrated hydrochloric acid or hydrazine.

Alternatively, the compounds of formula (4) can be reacted with an organolithium compound (e.g. phenyllithium or butyllithium) and subsequently reacted with a compound of formula (5). (See for example Aldrichimica Acta II, 15, (1978)).

The amines of formula (4) in which $R^1$ is halogen can be prepared by carrying out a Sandmeyer reaction on a 3-amino compound of formula (6):

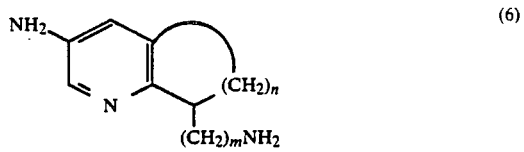

(6)

(in which m and n are as defined for formula (1)) that is by diazotisation of the amino group under strongly acidic conditions and displacing the diazo group with halo.

The amines of formula (2) in which $R^1$ is bromine can also be prepared by the direct bromination of the amines of formula (2) in which $R^1$ is hydrogen. Preferably the bromination is carried out with electrophilic bromine, for example using bromine in sulphuric acid.

The pyrimidone intermediates of formula (3) can be made by known methods as described in for example U.S. Pat. No. 4,145,546, U.S. Pat. No. 4,154,834 and European Patent Specification No. 17679.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium-free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of the Examples have $pA_2$ values greater than 7.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist. For the compounds of Examples 1, 2 and 4, the doses ($\mu$mol/kg) required to give a dose ratio of 11 ((DR-1)=10) are 0.022, 0.06 and 0.0048 respectively.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever rhinitis or allergic eczema.

Each dosage unit for oral administration contains preferably from 5 to 200 mg of a compound of formula (1) or a pharmaceutically acceptable salt thereof calculated as the free base.

The pharmaceutical compositions of the invention will normally be administered to a man for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

2-[3-(5,6,7,8-Tetrahydroquinol-8-yl)propylamino]-5-[1-oxopyrid-4-ylmethyl]-4(1H)-pyrimidone (a) 5,6,7,8-Tetrahydroquinoline (20 g) was added quickly to sodamide (17.6 g) in liquid ammonia (250 ml) to give a dark red coloured solution. 3-Chloropropylamine hydrochloride (28.9 g) was added in portions over four hours when loss of colour was permanent after which the reaction was stirred for a further 2 hours and then quenched with ammonium chloride (20 g). The liquid ammonia was allowed to evaporate and the residues were partitioned between chloroform and water. The pH was lowered to 6 and the chloroform layer was discarded. The aqueous layer was basified (pH 12–14), and extracted with chloroform, the chloroform extracts were dried, combined, evaporated and the residue was vacuum distilled to give 3-(5,6,7,8-tetrahydroquinol-8-yl)propylamine (7.58 g), b.p. 92°–94° C. at 0.1 mm Hg.

N.M.R. (CDCl$_3$, 250 MHz) assignment, δ (p.p.m.), multiplicity; 6,7-H tetrahydroquinolyl and —CH$_2$CH$_2$CH$_2$NH$_2$, 1.43–2.15, m; 5-H tetrahydroquinolyl and —CH$_2$NH$_2$, 2.75, m; 8-H tetrahydroquinolyl, 2.88, m; 3-H tetrahydroquinolyl, 7.01, m; 4-H tetrahydroquinolyl, 7.32, m; 2-H tetrahydroquinolyl, 8.39, m.

(b) 3-(5,6,7,8-Tetrahydroquinol-8-yl)propylamine (0.8 g) and 2-nitroamino-5-(1-oxopyrid-4-ylmethyl)-

4(1H)-pyrimidone (0.99 g) were refluxed in pyridine (2 ml) for six hours. The pyridine was removed in vacuo and the residue re-evaporated with n-propanol (2×30 ml) then chromatographed on silica in chloroform-methanol (4:1). The product was re-evaporated from ethanol to give the title compound as a glass (0.64 g).

N.M.R. (DMSO, 250 MHz) assignment, δ (p.p.m.), multiplicity; 6,7-H tetrahydroquinolyl and —CH$_2$CH$_2$CH$_2$NH, 1.40–2.07, m; 5,8-H tetrahydroquinolyl, 2.71, m; —CH$_2$CH$_2$CH$_2$NH, 3.25, m;

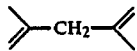

3.50, S; —CH$_2$NH—, 6.39, S; 3-H tetrahydroquinolyl, 7.06, m; 3,5-H pyridyl, 7.21, m; 4-H tetrahydroquinolyl, 7.40, m; 6-H pyrimidyl, 7.57, S; 2,6-H pyridyl, 8.05, m; 2-H tetrahydroquinolyl, 8.31, m; 1-NH pyrimidyl, 10.68, S.

EXAMPLE 2

2-[3-(5,6,7,8-Tetrahydroquinol-8-yl)propylamino]-5-(6-methylpyrid-3-ylmethyl)-4(1H)-pyrimidone A solution of 3-(5,6,7,8-tetrahydroquinol-8-yl)-propylamine (0.75 g, 0.0038 mole) and 2-nitroamino-5-(6-methylpyrid-3-ylmethyl)-4(1H)-pyrimidone (0.99 g, 0.0037 mole) in pyridine (1 ml) was refluxed for 8 hr and evaporated to dryness. The residue was chromatographed on silica in 10% MeOH/CHCl$_3$ then dissolved in hot CHCl$_3$, filtered, and the product precipitated with petroleum ether 40°–60° C. to give the title compound (0.38 g), m.p. 75°–80° C.

C$_{23}$H$_{27}$N$_5$O0.4H$_2$O: Found: C, 69.75; H, 7.08; N, 17.28; Requires: C, 69.43; H, 7.03; N, 17.60.

EXAMPLE 3

2-[3-(5,6,7,8-Tetrahydroquinol-8-yl)propylamino]-5-(6-methylpyrid-3-ylmethyl-N-oxide)-4(1H)-pyrimidone A solution of 3-(5,6,7,8-tetrahydroquinol-8-yl)-propylamine (2 g) and 2-nitroamino-5-(6-methylpyrid-3-ylmethyl-N-oxide)-4(1H)-pyrimidone (1.9 g) in pyridine (5 ml) was refluxed for 19 hr. and evaporated to dryness. The residue was chromatographed on silica in 20% MeOH/CHCl$_3$ and the required fractions were concentrated to dryness to give the title compound (2.62 g) as an amber foam.

EXAMPLE 4

2-[3-(5,6,7,8-Tetrahydroquinol-8-yl)propylamino]-5-(6-hydroxymethylpyrid-3-ylmethyl)-4(1H)-pyrimidone Trifluoroacetic anhydride (3.34 ml) was added to a suspension of 2-[3-(5,6,7,8-tetrahydroquinol-8-yl)propylamino]-5-(6-methylpyrid-3-ylmethyl-N-oxide)-4(1H)-pyrimidone (2.4 g) in dichloromethane (19 ml) giving a clear solution which was left sealed for 20 hr. under nitrogen. The reaction mixture was concentrated to dryness, re-concentrated with ethanol (2×50 ml) and the residues were then partitioned between chloroform and 10% sodium bicarbonate solution. The bicarbonate solution was extracted further with chloroform, the chloroform extracts were dried, combined and evaporated. The residue was chromatographed on silica in 20% MeOH/CHCl$_3$, then crystallised from acetonitrile/water 9:1 giving the title compound (0.66 g) m.p. indeterminate above 99°.

C$_{23}$H$_{27}$N$_5$O$_2$: Found: C, 67.99; H, 6.77; N, 17.16; Requires: C, 68.12; H, 6.71; N, 17.27.

N.M.R. (DMSO d$_6$, 250 MHz) assignment, δ (p.p.m.), multiplicity; 5,6,7-H tetrahydroquinolyl and —CH$_2$CH$_2$CH$_2$NH—, 1.35 to 2.10, broad m; 8-H tetrahydroquinolyl and —CH$_2$CH$_2$CH$_2$NH—, 2.71, m; —CH$_2$CH$_2$CH$_2$NH—, 2.23, m;

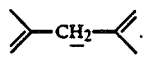

3.50, s;

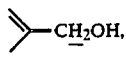

4.50, d;

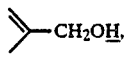

5.33, m; —CH$_2$CH$_2$CH$_2$NH—, 6.42, m; 3-H tetrahydroquinolyl, 7.08, m; 5-H pyridyl, 7.33, d; 4-H pyridyl, 7.42, m; 6-H pyrimidyl, 7.56, S; 4-H tetrahydroquinolyl, 7.59, m; 2-H tetrahydroquinolyl and 2-H pyridyl, 8.33, m.

EXAMPLE 5

A pharmaceutical composition for oral administration is prepared containing

| | | % by weight |
|---|---|---|
| A | 2-[3-(5,6,7,8-tetrahydroquinol-8-yl)-propylamino]-5-(6-hydroxymethylpyrid-3-ylmethyl-4(1H)—pyrimidone | 55 |
| | Dibasic calcium phosphate dihydrate | 20 |
| | Approved coloring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 6

A pharmaceutical composition for injectable administration is prepared by forming a solution of 2-[3-(5,6,7,8-tetrahydroquinol-8-yl)propylamino]-5-(6-hydroxymethylpyrid-3-ylmethyl-4(1H)-pyrimidone hydrochloride salt in sterile water to give a 1 to 5% w/w solution. The solution is clarified by filtration and filled into vials which are sealed and sterilised. A suitable vial contains 2 ml of the solution.

What is claimed is:

1. A compound of formula (1):

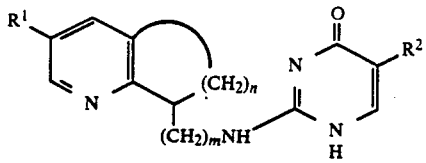 (1)

or a pharmaceutically acceptable acid addition salt thereof in which $R^1$ is hydrogen, $C_{1-4}$alkyl, $C_{1-4}$alkoxy, halogen or amino;

n is 2, 3 or 4;

m is 2, 3 or 4; and $R^2$ is hydrogen or $CH_2R^3$ where $R^3$ is hydrogen, $C_{1-6}$alkyl, or $C_{3-8}$cycloalkyl; phenyl optionally substituted by one or more $C_{1-6}$alkyl, $C_{1-6}$alkoxy, nitro or hydroxy groups or halogen atoms, or a methylenedioxy group; pyridyl or pyridyl-N-oxide optionally substituted by one or more $C_{1-6}$alkyl, $C_{1-6}$alkoxy, hydroxymethyl or hydroxy groups or halogen atoms; or a pyridone group in which the nitrogen atom is substituted by $C_{1-6}$alkyl.

2. A compound of claim 1 in which $R^1$ is hydrogen.

3. A compound of claim 1 in which n is 3.

4. A compound of claim 1 in which m is 3.

5. A compound of claim 1 in which $R^2$ is $CH_2R^3$.

6. A compound of claim 1 in which $R^3$ is 3-pyridinyl-N-Oxide, 6-methyl-3-pyridinyl-N-Oxide, 6-hydroxymethyl-3-pyridyl, 4,6-dimethyl-3-pyridinyl-N-Oxide, 6-hydroxymethyl-4-methyl-3-pyridyl, 5,6-dimethyl-3-pyridinyl-N-Oxide, 6-hydroxymethyl-5-methyl-3-pyridyl, 4-pyridinyl-N-Oxide, 6-methyl-3-pyridyl, or 1-methyl-2-oxo-pyrid-4-yl.

7. A compound according to claim 1 which is 2-((3-(5,6,7,8-tetrahydroquinolin-8-yl)propyl)amino)-5-((6-hydroxymethylpyridin-3-yl)methyl)pyrimidin-4-one or a pharmaceutically acceptable acid addition salt thereof.

8. A pharmaceutical composition having histamine $H_1$-antagonist activity comprising a histamine blocking effective amount of a compound according to claim 1 and a pharmaceutically acceptable carrier.

9. A method of blocking histamine $H_1$-receptors which comprises administering to a subject a non-toxic histamine blocking effective amount to block said receptors of a compound according to claim 1.

* * * * *